(12) United States Patent
Rouabhia et al.

(10) Patent No.: US 6,410,333 B1
(45) Date of Patent: Jun. 25, 2002

(54) ASSESSMENT OF HUMAN SKIN DAMAGE FOLLOWING EXPOSURE TO HARMFUL AGENTS

(75) Inventors: Mahmoud Rouabhia, Cap-Rouge; Régen Drouin, Québec; Marc Rhainds, Beauport; Joël Claveau, Cap-Rouge, all of (CA)

(73) Assignee: Université Laval, Québec (CA)

( * ) Notice: Subject to any disclaimer, the term of this patent is extended or adjusted under 35 U.S.C. 154(b) by 0 days.

(21) Appl. No.: 09/459,615

(22) Filed: Dec. 13, 1999

Related U.S. Application Data

(63) Continuation of application No. PCT/CA98/00609, filed on Jun. 15, 1998.

(30) Foreign Application Priority Data

Jun. 17, 1997 (CA) ............................................. 2207882

(51) Int. Cl.[7] ............................................. G01N 33/48
(52) U.S. Cl. ........................... 436/63; 436/64; 436/813; 435/29; 435/371; 600/306; 600/310; 600/556
(58) Field of Search ........................... 436/63, 64, 813; 435/4, 29, 30, 371; 600/306, 310, 556

(56) References Cited

U.S. PATENT DOCUMENTS

| 3,967,124 A | | 6/1976 | Strutz |
| 5,629,314 A | * | 5/1997 | Gaskin ........................ 514/256 |
| 5,691,158 A | * | 11/1997 | Reece et al. ................ 435/7.92 |
| 6,079,415 A | * | 6/2000 | Bernerd et al. ............. 128/898 |

FOREIGN PATENT DOCUMENTS

| EP | 358 506 A | | 9/1989 |
| EP | 497399 | * | 8/1992 |
| FR | 2 689 904 A | | 10/1993 |
| WO | WO 91 16010 A | | 10/1991 |

OTHER PUBLICATIONS

Preston DS et al., 1992, *N. Engl. J. Med.*, 327: 1649–1662.
Young, AR, 1990, *Semin. Dermatol.*, 9(1): 25–31.
Frederick JE et al., 1989, *Photochem. Photobiol.*, 51:443–450.
Kligman AM, 1969, *JAMA*, 210:2377–2380.
Gilchrest BA et al., 1983, *J. Am. Acad. Dermatol.*, 9: 213–219.
Garmyn M et al., 1995, *Dermatology*, 190: 305–308.
Jeevan A et al., 1993, *The Lancet*, 342: 1159–1161.
Stern RS et al., 1986, *Arch Dermatol.*, 122: 537–545.
Jarratt M et al., 1983, *J. Am. Acad. Dermatol.*, –9: 354–362.
Pathak M, 1985, *Ann. NY Acad. Sci.*, 453: 328–339.
Groves AG, 1990, In Sunscreens Development, evaluation, and regulatory aspects (eds) Nicholas J Lowe and Nadim A Shaath. Marcel Dekker, Inc New York: 411–420.
Beitner H, 1988, *Photodermatology*, 5: 96–100.
Kaidbey KH et al., 1978, *J. Invest. Dermatol.*, 72: 253–256.
Lowe JN et al., 1980, *J. Invest. Dermatol.*, 74: 181–182.
Freeman SE et al., 1988, *Photodermatology*, 5: 243–247.
Bridges B et al., 1980, *Nature*, 283: 523–524.
Wolf P et al., 1993, *J. Invest. Dermatol.*, 101: 523–527.
Rouabhia M et al., 1994, *Cell. Transplantation*, 3(6): 529–536.
Pâquet I et al., 1996, *J. Cell. Physiol.*, 166: 296–304.
Rouabhia M. et al., 1993, *Transplantation*, 56(2): 259–264.
Drouin R. et al., 1986, In technologies for detection of DNA damage and mutations,edited by Pfeifer GP, Plenum Press, New York: 37–43.
Pfeifer GP et al., 1993, *Mutation Research*, 288: 39–46.
Sutherland et al., 1986, *Chemincal Abstract*,104 (13), Abstract 105139.

* cited by examiner

*Primary Examiner*—Maureen M. Wallenhorst
(74) *Attorney, Agent, or Firm*—Ogilvy Renault; France Côté; Christian Cawthorne

(57) ABSTRACT

The present invention relates to the assessment of ultraviolet radiation UV effects on sunscreen-treated and non-treated human skin using a more sensitive technique.

29 Claims, 4 Drawing Sheets

ASSESSMENT OF HUMAN SKIN DAMAGE FOLLOWING EXPOSURE TO HARMFUL AGENTS

This application is a continuation of PCT/CA98/00609 filed Jun. 15, 1998 designating the United States and claiming priority of Canadian Patent Application Serial No. 2,207,882 filed Jun. 17, 1997.

BACKGROUND OF THE INVENTION (a) Field of the Invention

The present invention relates to the assessment of ultraviolet radiation UV effects on sunscreen-treated and non-treated human skin using a more sensitive technique. In particular, the Invention relates to:

- the production of human skin substitutes containing keratinocytes, melanocytes, fibroblasts and dermal extracellular matrix;
- the protection of human skin surface with a sunscreen using standard quantity (2 ml/cm$^2$);
- the irradiation of these treated and non-treated skin substitutes using UVA, UVB and simulated sunlight ultraviolet sources;
- the analyses of the sunscreen effects on non-irradiated cutaneous cells and extracellular matrix; and
- the analyses of he harmful effects of these UV irradiations on skin structure and the photo-induced DNA damage before and after sunscreen protection.

(b) Description of Prior Art

A sunny day generally puts people in a very good mood. Indeed, all of us look forward to outdoor activities in summer. Outdoor activities mainly depend on warm and sunny weather conditions. The sun seems to be innocuous for the vast majority of the world's population. In fact, the sun simply provides life-sustaining heat, light and energy. However, solar irradiation causes a large variety of harmful effects including photoaging and skin cancers (Preston D S et al., 1992, *N. Engl. J. Med.,* 327:1649–1662).

The sun is the main source of UV radiation (Young A R, 1990, *Semin. Dermatol.,* 9(1):25–31). The broad spectrum and intensity of UV light from the sun are due to the high temperature on the earth's surface and its size. The intensity of solar UV reaching the earth is certainly highly dangerous and would probably be lethal to the majority, if not all living organisms on the earth's surface, without the shielding afforded by ozone layer. The UV solar spectrum is divided into three categories.

Ultraviolet-C (UVC) radiation ranges from 200 to 280 nm and is completely absorbed by the earth's ozone layer. Ultraviolet-B (UVB) radiation ranges from 280 to 320 nm. A significant amount is absorbed by the ozone layer. This type of radiation causes most sunburn, redness and skin cancer. Ultraviolet-A (UVA) radiation ranges from 320 to 400 nm. As opposed to UVC and UVB, very little of this UVA radiation is absorbed by the ozone layer. The UVA dose reaching the earth is 100 to 1,000 times higher than UVB radiation (Frederick J E et al., 1989, *Photochem. Photobiol.,* 51:443–450).

Skin is exposed to UV radiations from birth to death. Although, there are few beneficial effects of exposure to UV light, most of their effects are deleterious to human skin and eyes (Kligman A M, 1969, *JAMA,* 210:2377–2380). The harmful effects of sunlight exposure result in erythema, accelerated skin aging, pigmentation anomalies, actinic keratosis, immunosuppression, DNA damage and skin cancers (Preston D S et al., 1992, *N. Engl. J. Med.,* 327:1649–1662; Garmyn M et al., 1995, *Dermatology,* 190:305–308; Jeevan A et al., 1993, *The Lancet,* 342:1159–1161). Basic and clinical literature have incriminated both UVA and UVB on these different skin pathologies. Efforts to increase scientific knowledge regarding the photobiologic effects of UV light on the skin are important and relevant to both prevention and treatment of many human skin diseases.

The increasing need for sun protection agents to be used by the general population around the world has become evident over the last decade. In a population that spends more recreational time in the sun, there is a growing awareness regarding the protection of these people against the harmful effects of UV. The use of sunscreen designed to protect them has increased dramatically in the past decades (Stern R S et al., 1986, *Arch Dermatol.,* 122:537–545). The generally accepted parameter for evaluating the efficacy of sunscreen preparations against UV radiation is the sun protection factor (SPF) (Jarratt M et al., 1983, *J. Am. Acad. Dermatol.,* 9:354–362). The endpoint for the determination of a sunscreen SPF is the appearance of erythema which is related to protection against sunburn. The erythemal phase is evaluated 24 hrs following the irradiation protocol and calculated using the below defined formula:

$$SPF = \frac{\text{Minimal erythema dose } (J/cm^2) \text{ in sunscreen protected skin}}{\text{Minimal erythema dose } (J/cm^2) \text{ in non-sunscreen protected skin}}$$

UVB radiations are most effective for producing tanning as well as erythema (Pathak M, 1985, *Ann. NY Acad. Sci.,* 453:328–339) and SPF values reflect the degree of protection against this UVB radiation. Recently produced sunscreens cover a wider UV spectrum to protect skin from ultraviolet irradiation including UVA. The evaluation of a sunscreen efficacy is based on SPF method. However, for different reasons this method cannot be used successfully as an endpoint in determining the efficacy of a sunscreen for blocking the UVA harmful effects.

UVA necessitate prolonged exposure period to initiate erythema in normal skin. To use the erythemal reaction as an indication of effectiveness against UVA radiation and to expedite the determination, the skin must be sensitized by the application of a phototoxic chemical prior to exposure to the UVA radiation. Since many of these chemicals are carcinogenic, using this technique is presently prohibited for ethical reasons (Groves A G, 1990, In *Sunscreens Development, evaluation, and regulatory aspects* (eds) Nicholas J Lowe and Nadim A Shaath. Marcel Dekker, inc New York:411–420).

Other possible endpoints for evaluating UV protection and basically UVA protection include immediate and delayed pigmentation. Immediate pigment darkening (IPD) is an oxygen-dependent photochemical reaction of melanin or its precursors in existing melanosomes (Beitner H, 1988, *Photodermatology,* 5:96–100). The response is a gray-brown pigmentation which appears during or immediately after irradiation and fades over a period ranging from a few minutes to a few hours (Kaidbey K H et al., 1978, *J. Invest. Dermatol.,* 72:253–256). Delayed pigmentation (tanning) represents proliferation of melanocytes and increased production of melanosomes.

However, to get a complete efficacy against UVA and UVB radiations, the sunscreen must protects also against photoaging, DNA damage and skin cancers (Lowe J N et al., 1980, *J. Invest. Dermatol.,* 74:181–182; Freeman S E et al., 1988, *Photodermatology,* 5:243–247).

The sunscreen predictive actions are generated using human volunteers (Lowe J N et al., 1980, *J. Invest. Dermatol.*, 74:181–182). Unfortunately, these evaluations were costly, difficult and suspicious upon the development of hyperpigmented areas subsequent to UV exposure (Bridges B et al., 1980, *Nature*, 283:523–524).

To overcome these limitations, experimental models (rats, mice, etc.) were used for photodermatological studies (Wolf P et al., 1993, *J. Invest. Dermatol.*, 101:523–527). Despite many similarities, the use of animal skin to elucidate mechanisms of UV-induced damage in human cutaneous tissues is hampered by inherent biological differences. Consequently, scientists are still looking for the appropriate model to:

1—understand the different mechanisms involved in skin damage after UV radiation, 2—be used for sunscreen testing;

3—be used as a more sensitive and effective method for UV harmful effect assessment and sunscreen efficacy concerning skin cancer prevention.

Regarding the third point, as the erythemal phase is due to the penetration into the skin of an important UV radiation dose which induces an inflammatory reaction first, and then erythema. Our concern is that prior to the suberythemal phase, UV radiation has already caused histological perturbations to the skin and DNA damage to the cutaneous cells (keratinocytes, melanocytes, etc.) which precede skin cancer. Consequently, it is mandatory to develop a more sensitive method that allows UV damage assessment before getting to the erythemal phase.

One of our interests is to devise a more sensitive method for skin protection against harmful UVA and UVB effects. This critical goal may be attained with the invention described below.

SUMMARY OF THE INVENTION

The present invention relates to a process of producing in vitro skin substitutes containing human fibroblasts included into a collagen gel over-layered with human keratinocytes. After 20 days of culture, these skin substitutes were either treated or non-treated with a sunscreen (applied on the epidermal surface), then exposed or not to UVA, UVB and simulated sunlight (UVA-UVB). A novel aspect of the invention is the correlation between structural damage on the skin substitutes and the DNA damage in the cells after each type of irradiation. These assessing methods (structural and DNA damage methods) are applicable to UVA, UVB and simulated sunlight harmful effect analyses. Furthermore, due to its high sensitivity, this DNA damage method is also useful to assess the deleterious effects of other rays such as X-ray and infrared wavelengths. This method is also useful to assess the toxicity of different chemicals and other products. Using these methods we will be able to draft new legislation dealing with a cancer protective factors as a criterion for predicting the ability of a sunscreen to provide protection against ultraviolet radiations (UVA, UVB, UVC).

It is predicted that using DNA damage would help in the determination of the real damage induced to the cells and the capacity of these chemical and physical toxic exposed cells to repair, die or mis-repair without death (mutations) leading to skin cancer.

Skin substitutes are very useful for UV effect assessment on cutaneous cells and extracellular matrix. Indeed, skin substitutes can be produced at large. Their use provides more effective and repeated results. Finally, skin substitutes avoid the use of human volunteers to assess the efficacy of sunscreen. Accordingly, after skin substitute production and irradiation, the DNA damage analysis provides a very sensitive method to assess the capacity of the skin to support one or the other ultraviolet doses.

The DNA damage analysis method provides a more sensitive way to assess the capacity of a sunscreen on preventing DNA damage in UVA, UVB, UVC and simulated sunlight irradiated skin.

The DNA damage analysis method also provides a very sensitive way to assess the capacity of a sunscreen in preventing DNA damage in X-ray and infrared wavelength damaged skin.

In addition, the DNA damage analysis method provides a more sensitive way to assess the toxicity of chemical in the skin.

DETAILED DESCRIPTION OF A PREFERRED EMBODIMENT

Figure 1:
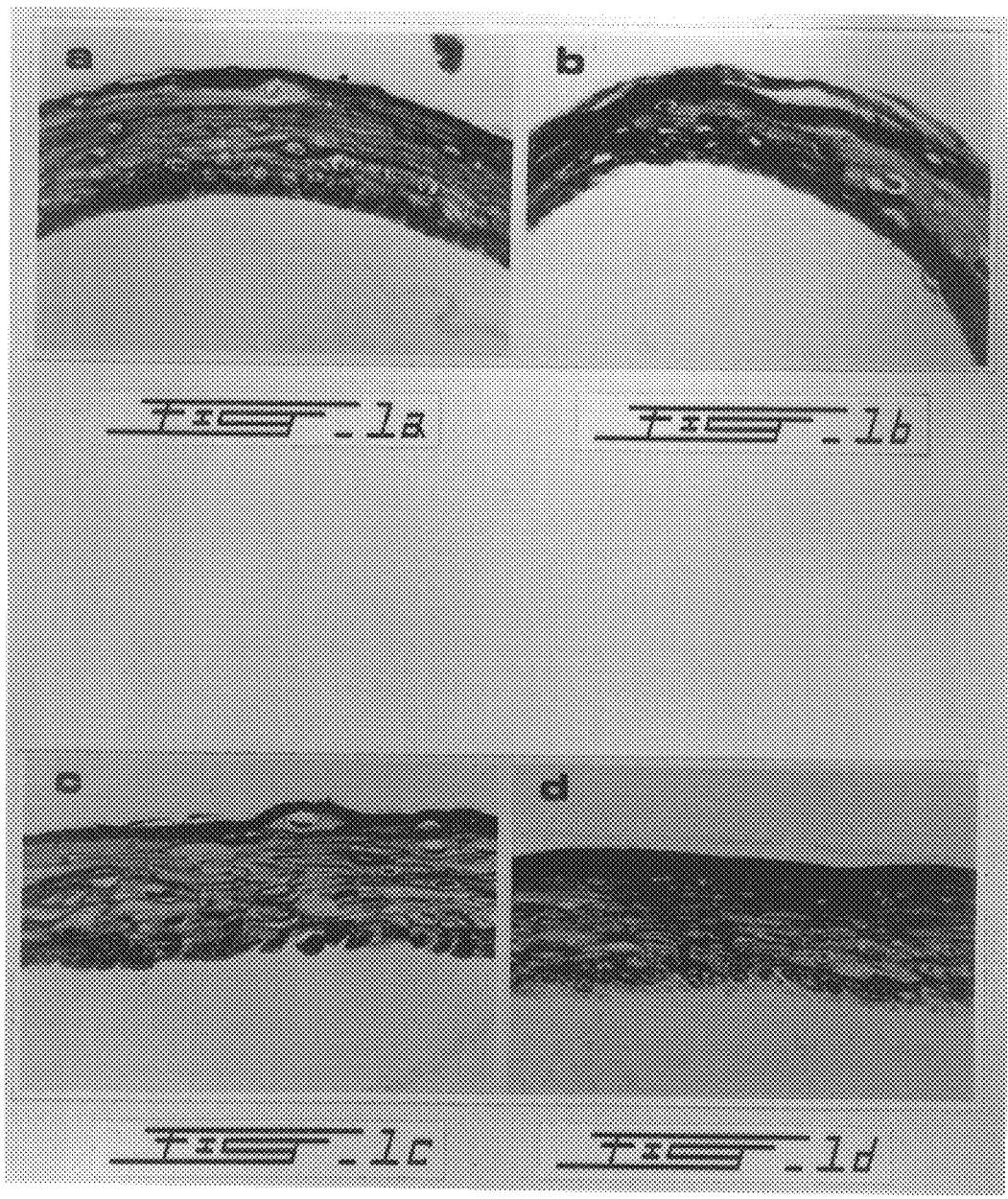
FIGS. 1$a$–1$d$ illustrate the histological structure of the epidermis after protection with a sunscreen (SPF 15) and then simulated sunlight irradiation.

The following is a description, by way of example, of one embodiment of the present invention wherein human skin substitutes are prepared and used to assess the UVA, UVB and simulated sunlight radiation effects on skin structure and DNA damage.

Human Keratinocyte and Fibroblasts Isolation

Keratinocytes and fibroblasts were isolated from human skin biopsies as previously described (Rouabhia M et al., 1994, *Cell Transplantation*, 3(6):529–536). Briefly, after the dermal layer was trimmed, the skin biopsy was cut into 5 mm×5 mm pieces and then digested in a 500 mg/ml thermolysin solution (Sigma Chemical Co., St Louis, Mo., USA) overnight at 4° C. This treatment allowed complete separation of the epidermis from the dermis.

The epidermis was cut into small pieces and incubated with 0.05% trypsin-0.1% EDTA in phosphate-buffered saline (PBS) for 30 min. at 37° C. Cell suspensions were collected in tubes containing an equal volume of culture medium with 10% FCS to neutralize the protease activity. Keratinocytes were washed twice and resuspended in culture medium. A trypan blue exclusion method was used to assess cell viability.

The dermis was cut into small pieces and incubated with collagenase (0.1%) in culture medium for 90 min. at 37° C. Cell suspensions were collected in tubes containing an equal volume of culture medium with 10% FCS to neutralize the collagenase activity. Fibroblasts were washed twice and resuspended in culture medium. A trypan blue exclusion method was used to assess cell viability.

Human Keratinocyte and Fibroblast Cultures

Both cell types were plated into culture flasks (Falcon, Becton Dickinson, Lincoln Park, N.J., USA). Keratinocytes were seeded at $7\times10^5$ cells / 75 cm$^2$ flask with lethally irradiated (6000 rad) mouse 3T3 fibroblasts as feeder cells in DMEM-supplemented medium as previously described (Rouabhia M et al., 1994, *Cell Transplantation*, 3(6):529–536). Fibroblasts were seeded at $10^6$ cells/flask in DME-supplemented medium. The medium was changed three times a week. Cultures were routinely checked for mycoplasma contamination. When the cultures reached 80 to 90% confluence, cells were detached from the culture flasks with trypsin-EDTA, washed twice and resuspended in DMEM or DMF-supplemented media and used for the production of skin substitutes.

Skin Substitute Production

Skin substitutes were produced by seeding human skin fibroblasts into a collagen matrix as previously described (Pâquet I et al., 1996, *J. Cell Physiol.*, 166:296–304). Briefly, collagen (2 mg/ml) was mixed with human fibroblasts ($1.5\times10^5$ cells) and poured into a petri dish (35-mm diam) to produce the dermal substitutes. To prevent collagen lattice contraction a 5 mm-wide ring of unglued filter paper (Whatman, Maidstone, U.K.) was used as a peripheral anchor according to a previously described method. These dermal substitutes were cultured in 10% FCS-supplemented culture medium and incubated in a humidified atmosphere at 37° C. Four days later, human keratinocytes ($9\times10^4$/cm$^2$) were seeded onto the dermal substitutes and grown under submerged conditions until the epidermal layer covered the total surface of the dermal substitute. This complete confluence was reached after 10 days of culture. Skin substitutes were then cultured for 5 more days on an air-liquid interface which allowed the formation of the stratum corneum. At this time, all skin substitutes were ready for sunscreen treatment and UV irradiations. Before their irradiation, skin substitutes were treated with an SPF 15 sunscreen (which contains as active ingredients: Butyl Methoxydibenzoylmethane, Octyl Methoxycinnamate, Benzophenone 3) or an SPF 30 sunscreen (which contains as active ingredients: Butyl Methoxydibenzoylmethane, Octyl Methoxycinnamate, Salicylate, Oxybenzone). To do so, the upper layer (stratum corneum) of the epidermis of each skin substitute was covered with each sunscreen (2 ml/cm$^2$) for 30 min. before their irradiation. These sunscreen treated skin substitutes were compared to non-treated skin substitutes (control experiments). These skin substitutes were then irradiated using UVA, UVB and simulated sunlight sources.

Skin Substitute Irradiation

For the UV exposure, the culture medium was replaced by pre-warmed saline solution (only the dermal structure was covered) to avoid the formation of medium-derived toxic photoproducts. Thirty minutes after sunscreen treatment, or not, skin substitutes were exposed, or not, to UV emitters.

UVA irradiation: light was provided by a bank of two Philips black light bulbs (BLB18, 15W). Each skin substitute received a single dose of UVA (500 KJ/m$^2$). This dose was chosen to fall within the UVA dose received after 2 hours exposure to the sun in the Zenith in Quebec.

UVB irradiation: light was provided by a bank of two Philips UVB bulbs (FS20T12UVB/BP). Each skin substitute received a single dose of UVB (50 KJ/m$^2$).

UVA and UVB irradiation: light was provided by a simulated sunlight, which provides light of 290–400 nm with a spectral distribution similar to sunlight. Each skin substitute received a single dose ($4\times10^6$ J/m$^2$) of UVA-UVB. This UV dose contain basically 10 to 15% of UVA and 5% of UVB.

Sham-irradiated skin substitutes were handled identically, but placed under a dark cloth adjacent to he ultraviolet beam.

Immediately after irradiation, the epidermal part of each skin substitute was separated mechanically from the dermal part. A reduced number (3 to 4) of biopsy specimens were harvested for histological studies. What was left from each epidermis was incubated for 30 min. in a trypsin solution to make cell suspension for DNA photodamage analyses.

Histological Analyses

For histological studies, biopsies were taken from irradiated (sunscreen treated, or not) and non-irradiated (sunscreen treated, or not) skin substitutes. Samples were fixed in Bouin's solution for 24 h and embedded in paraffin. Thin cryostat sections (4 mm) were prepared from each biopsy. Masson trichrome staining was used to evaluate the histology of these different materials. Sections were mounted and observed as previously described (Rouabhia M et al., 1993, *Transplantation*, 56(2):259–264).

DNA Damage Analyses

Physical and chemical mutagens induce frank breaks in DNA which reduce its single-strand molecular weight. Other non-break lesions in the DNA can often be converted into strand breaks by chemical and enzymatic means. Using agarose gel electrophoresis along with various cleavage schemes, the average density of breaks and various lesion classes along mammalian DNA can be determined. For this reason, after UVA, UVB and simulated sunlight irradiation, keratinocytes were isolated and prepared for DNA photodamage analyses. After DNA extraction, an alkaline 1.2% agarose gel was used to estimate the global frequency of cyclobutane pyrimdine dimers (CPD) and pyrimidine (6–4) pyrimidane photoproducts. Also, glyoxal electrophoresis gel method was used to estimate global frequency of photo-oxydative damage induced by these different irradiations. To do so, agarose gel was prepared as previously described, and DMSO treated DNA was loaded, gel was run, stained and destained as previously described (Drouin R et al., 1986, *In technologies for detection of DNA damage and mutations*, edited by Pfeifer G P, Plenum Press, New York:37–43; Pfeifer G P et al., 1993, *Mutation Research*, 288:39–46).

Photodamages have been enzymatically converted to single-strand breaks. Indeed, CPD frequency is enzymatically converted to single-strand breaks with T4 endonuclease V. Also, 6–4 photoproducts can be chemically converted to single-strand breaks using hot piperidine or enzymatically converted using UvrABC. Finally, photo-oxydative lesions are converted using Nth protein and Fpg protein of *E. coli* (Table 1).

TABLE 1

Enzymes used to convert photodamages to single-strand breaks

| PHOTOPRODUCTS | CONVERTED ENZYME |
| --- | --- |
| CPD | T4 endonuclease-V |
| 6-4 Photoproducts | hot piperidine or UvrABC |
| Photo-oxydative product | Nth and Fpg proteins |

Results

The inventors have developed a new procedure to assess the deleterious effects of ultraviolet exposure on mammalian cells based on the DNA damage quantification. This procedure should be used for effective damage analyses of each cell type which has been exposed to UVA, UVB, UVC, infrared wavelengths, X-ray, chemical products, etc.

Figure 3:
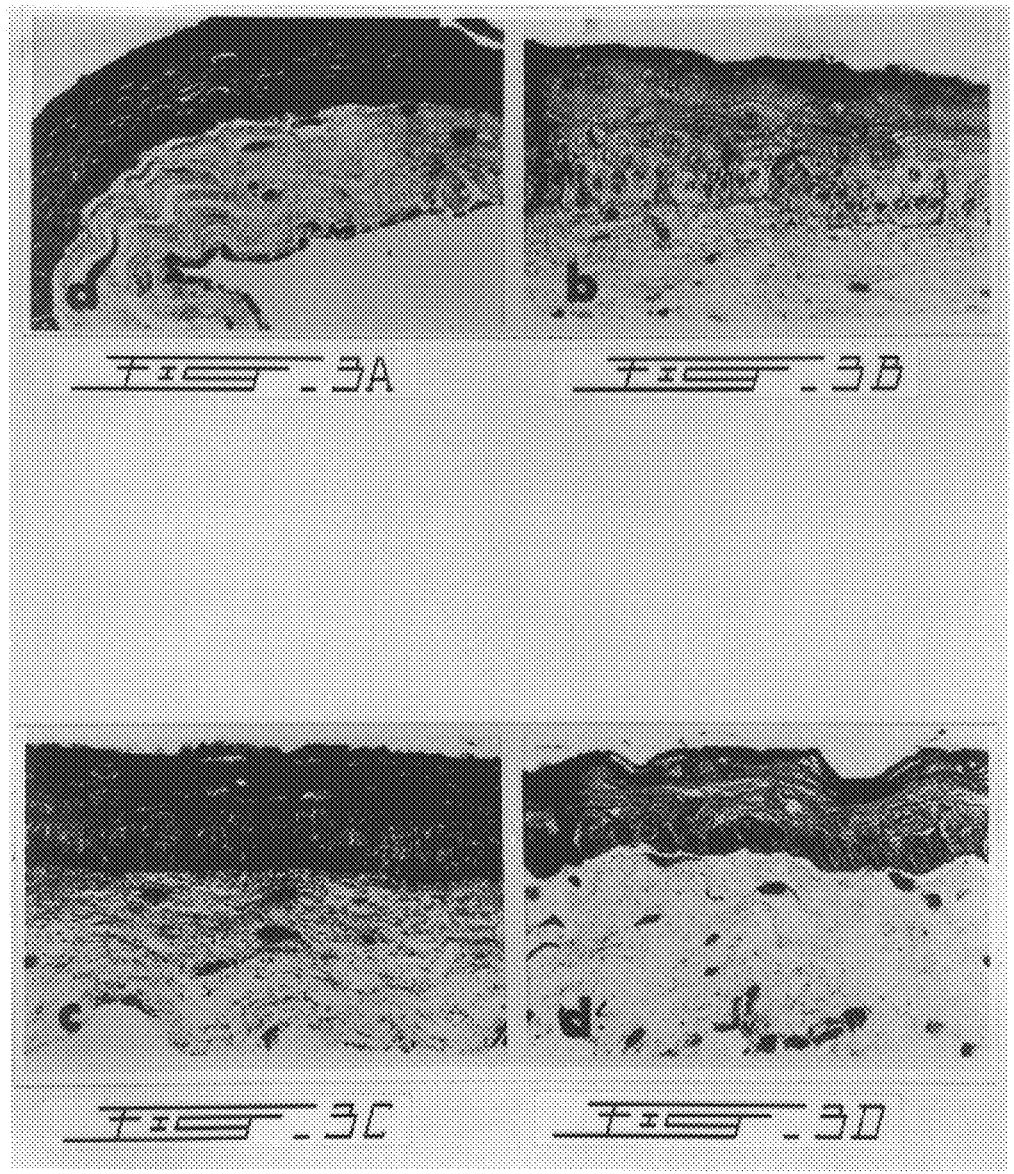
FIGS. 3$a$–3$d$ illustrate the histological structure of the epidermis after protection with a sunscreen (SPF 30) and then irradiated using simulated sunlight sources.

Skin substitutes were produced by including fibroblasts in a collagen gel (extracellular matrix). Four days later this gel was over-layered with human keratinocytes and cultured until these keratinocytes reached their confluence. Skin substitutes were then maintained at an air-liquid interface for 5 days. This air-liquid procedure allowed the formation of an appreciable cornification of the epidermal upper layers (FIGS. 1 and 3). After their sunscreen treatment for 30 min. and then irradiation using UVA, UVB or simulated sunlight we performed histological analyses.

FIGS. 1 and 3 show the cutaneous structures after UV irradiation. Skin substitutes were produced, then treated or non-treated with 2 ml/cm$^2$ of sunscreen (SPF 15 or SPF 30).

After 30 min. treatment with a sunscreen, each skin substitute was irradiated using simulated sunlight. Immediately after irradiation, biopsy specimens were harvested from the tissue of each skin substitute and stained using Masson trichrome. Panels (FIGS. 1 and 3; c, b) show the non-irradiated tissues and panels (FIGS. 1 and 3; c, d) showed irradiated tissues. Panels (FIGS. 1 and 3; a, c) represent non-treated tissues, panels (FIGS. 1 and 3; b, d) represent sunscreen treated tissues.

In FIGS. 1 and 3 we note that, the irradiated, but non-sunscreen protected epidermis was significantly damaged. Indeed, all epidermal layers (basal to cornified layers) were affected. There was a real structural dysfunction of the epidermis with the presence of "sun-burn" cells and a large number of differentiated keratinocytes even in the basal layer where we are supposed to have only small and cuboidal proliferative keratinocytes. When the sunscreen was used, the deleterious effects of UV were significantly reduced, but not completely prevented. Indeed, we can appreciate the well organized epidermal structure with different multilayers. These structures showed a well organized basal layer with small cuboidal keratinocytes and different stratified layers. These structures were comparable to those obtained from non-irradiated and sunscreen treated, or not, skin substitutes.

As a summary to these histological studies, skin substitute allowed for a real analyses of the structural defects induced by the UV on the epidermal structure. These histological studies also demonstrate the efficacy of the sunscreen treatment on the reduction of ultraviolet deleterious effects. It is a great improvement in the field of histological perturbation following ultraviolet irradiation compared to erythemal assessment which is a subjective method (based on the observer bias).

Figure 2:
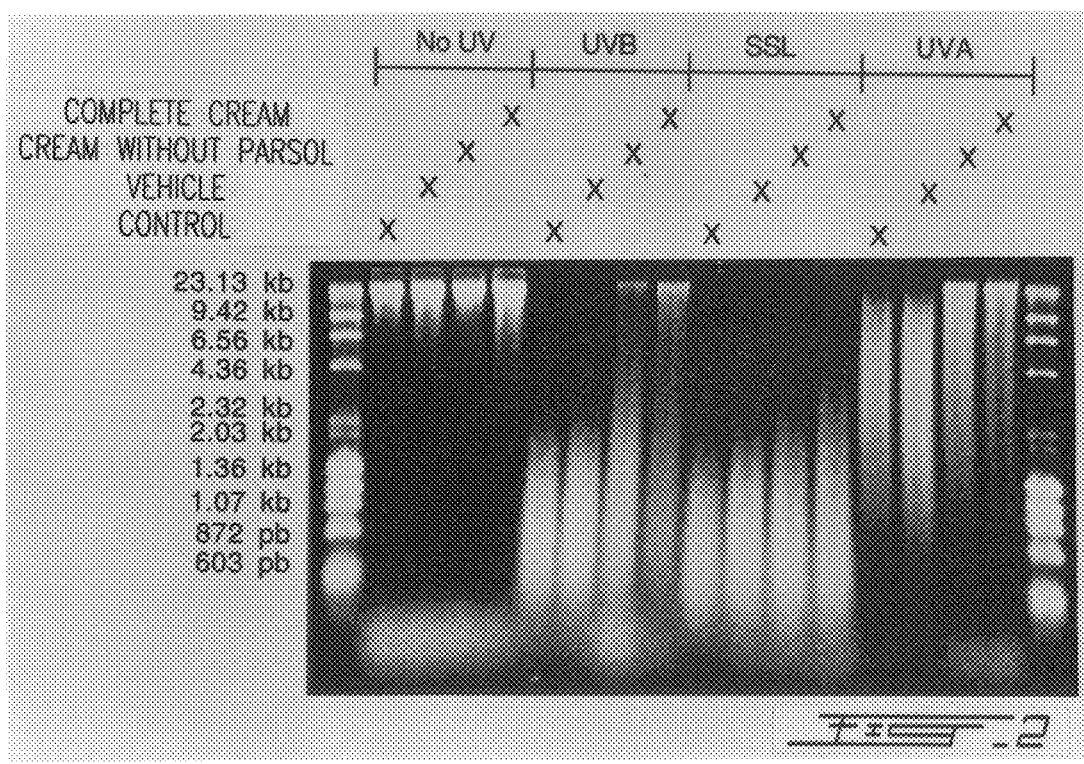
FIG. 2 illustrates the cyclobutane pyrimidine dimers (CPD) frequency on the damaged DNA after skin substitute protection by a sunscreen (SPF 15) then irradiation using UVA, UVB and simulated sunlight sources.
Figure 4:
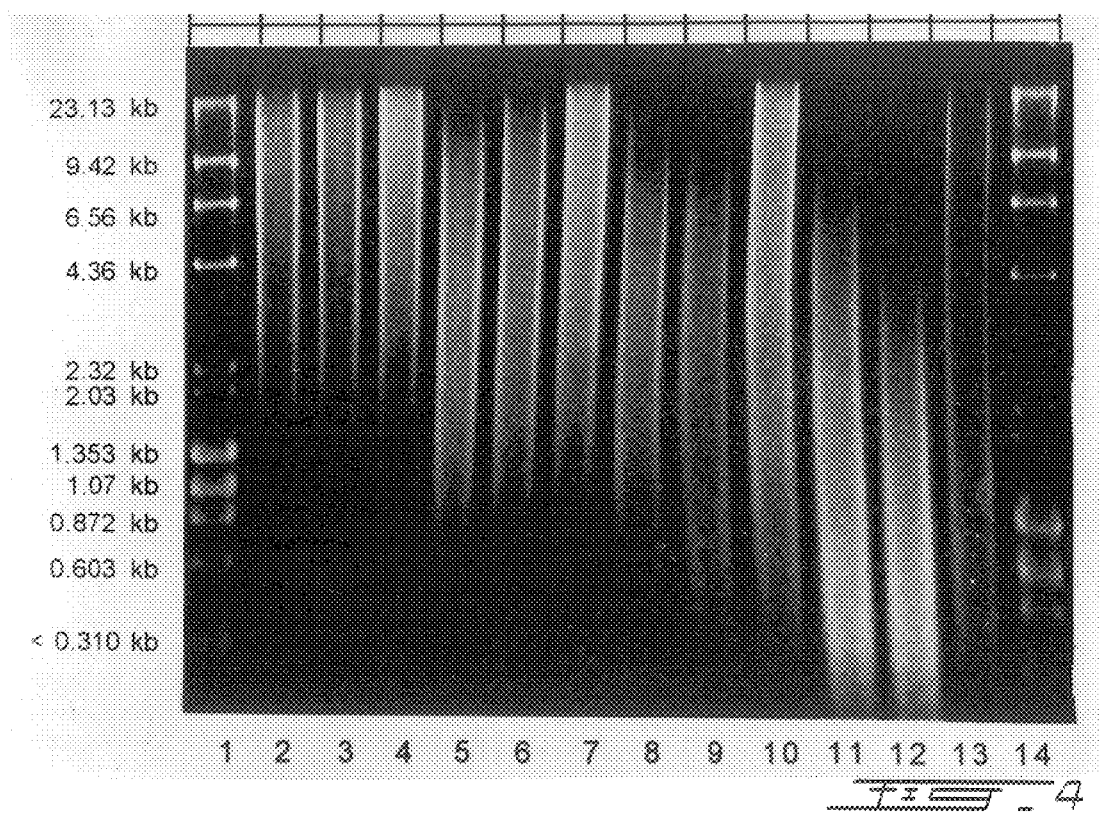
FIG. 4 illustrates the pyrimidine (6–4) pyrimidane photoproduct frequency on the damaged DNA after skin substitute protection by a sunscreen (SPF 30) then irradiated using simulated sunlight sources.

These histological defects were correlated with DNA photodamage FIGS. 2 and 4. As shown in FIG. 2 and Table 2, the frequency of DNA damage as judged by photoproducts in UVA irradiated non sunscreen treated skin substitutes, was about 4.6 photoproducts/10 kb. This frequency was significantly reduced (0.75 photoproducts/10 kb) with SPF 15 sunscreen treatment. Comparative results were obtained with SPF 30 sunscreen (FIG. 4).

FIG. 2 and Table 2 CPD have been enzymatically converted to single strand breaks with T4 endonuclease V and photoproducts have been chemically converted to single-strand breaks with hot piperidine. In FIG. 2, CPD was presented on lines 14 to 17 after UVA irradiation,, lines 6 to 9 for UVB irradiation and lines 10 to 13 for simulated sunlight irradiation. Quantitatively, these CPD products are summarized in Table 2.

TABLE 2

Quantitative determination of the cyclobutane pyrimidine dimers (CPD) frequency in the keratinocyte damaged DNA after skin substitute irradiation

| Irradiation | No Sunscreen | With Sunscreen (SPF 15) |
|---|---|---|
| None | 0.5 | 0.5 |
| UVA | 4.6 | 0.75 |
| UVB | 35 | 10 |
| Simulated sunlight | 40 | 15 |

After UVB irradiation, in non-protected skin substitutes with sunscreen, the frequency of DNA damage was about 35 cyclobutane pyrimidine dimers (CPD)/10 Kb. However, after sunscreen treatment, this frequency drops significantly to 10 CPD/10 Kb.

Using simulated sunlight (UVA-UVB) irradiated skin substitutes the frequency of DNA damage of non-protected tissue was about 40 CPD/10 Kb. This frequency was significantly reduced (15 CPD/10 Kb) after sunscreen treatment.

To estimate the various breaks in the DNA, we realized a glyoxal electrophoresis gel, non-sunscreen treated skin equivalent but UVA, UVB or simulated sunlight irradiated showed significant and various breaks in the DNA when compared to sunscreen treated cells. Both DNA damage analyses, correlated with the histological analyses. They therefore, showed a UVA and UVB harmful effect on the skin structure and on the DNA.

Consequently, our new procedure is useful to evaluate sunscreen efficacy regarding skin cancer prevention and should be labeled: Cancer Protection Factor (CPF). It is then predicted that using this technology, could significantly assist the sunscreen industry in developing a more effective protection for humans against UV irradiation and other environmental agents. This technology could also contribute to cutaneous cancer prevention and even treatment if we understand the mechanisms involved in its development. While the above description relates to histological and DNA damage assessment after UVA, UVB and simulated sunlight irradiation, it is predicted that this technology could also be used to assess structural and molecular damage after contact with chemical products, ionizing irradiations, infrared wavelengths, etc.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A process to assess the efficacy of a sunscreen preparation against harmful effects of environmental agents, which comprises the steps of:
   a) providing human cutaneous cells and extracellular matrix in in vitro cultured conditions;
   b) treating said human cutaneous cells and matrix of step a) with a sunscreen;
   c) submitting said treated human cutaneous cells and matrix of step b) to at least one environmental agent for a period of time sufficient to induce structural damage and DNA damage;

d) measuring said structural damage and said DNA damage of step c); and e) correlating said measuring of step d) with the efficacy of said sunscreen.

2. The Process according to claim 1, wherein said human cutaneous cells are selected from the group consisting of human keratinocytes, human melanocytes and human fibroblasts.

3. The process according to claim 2, wherein said human fibroblasts are mixed with collagen gel to produce in vitro a dermal substitute.

4. to The process according claim 3, wherein collagen gel is a dermal extracellular matrix.

5. The process according to claim 2, wherein said human keratinocytes are seeded onto a dermal substitutes to obtain skin substitutes.

6. The process according to claim 5, wherein said skin substitutes are cutaneous tissues.

7. The process according to claim 5, wherein said skin substitutes are used for skin damage analyses in the method.

8. The process according to claim 7, wherein said skin damage is due to environmental agents which comprise chemical products and agents causing cutaneous pathologies.

9. The process according to claim 8, wherein cutaneous pathologies are selected from the group consisting of dermatitis, psoriasis and melanomas.

10. The process according to claim 8, wherein environmental agents also comprise ultraviolet radiations, X-ray or infrared wavelengths.

11. The process according to claim 10, wherein ultraviolet radiations are ultraviolet-A (UVA), ultraviolet-B (UVB) or ultraviolet-C (UVC).

12. The process according to claim 7, wherein skin damage involves structural and DNA damage.

13. The process according to claim 12, wherein structural damage is at the level of the epidermal and dermal cells, and extracellular matrix perturbations.

14. The process according to claim 12, wherein DNA damages are keratinocyte, melanocyte or fibroblast DNA damage.

15. The process according to claim 14, wherein DNA damage involves an assessment of cyclobutane pyrimidine dimer (CPD) formation and the distinction of various classes of breaks in the damaged DNA.

16. The process according to claim 15, wherein the assessment of CPD formation is carried out using alkaline electrophoresis gel.

17. The process according to claim 15, wherein DNA breaks assessment is carried out using glyoxal electrophoresis gel.

18. The process according to claim 14, wherein DNA damage is due to UVA irradiation.

19. The process according to claim 14, wherein DNA damage is due to UVB irradiation.

20. The process according to claim 14, wherein DNA damage is due to simulated sunlight irradiation.

21. The process according to claim 14, wherein DNA damage is due to infrared wavelengths.

22. This process according to claim 14, wherein DNA damage is due to X-ray exposition.

23. The process according to claim 12, wherein said structural damage is due to UVA irradiation.

24. The process according to claim 12, wherein said structural damage is due to UVB irradiation.

25. The process according to claim 12, wherein said structural damage is due to simulated sunlight irradiation.

26. The process according to claim 12, wherein said structural damage is due to infrared wavelengths.

27. The process according to claim 12, wherein structural damage is due to X-ray exposure.

28. The process according to claim 12, wherein structural and DNA damage is due to chemical products.

29. The process according to claim 1, wherein said human cutaneous cells are selected from the group consisting of epidermal and dermal cells.

* * * * *

UNITED STATES PATENT AND TRADEMARK OFFICE
CERTIFICATE OF CORRECTION

PATENT NO. : 6,410,333 B1
DATED : June 25, 2002
INVENTOR(S) : Mahmoud Rouabhia et al.

It is certified that error appears in the above-identified patent and that said Letters Patent is hereby corrected as shown below:

Column 1,
Line 20, replace "2ml/cm$^2$" by -- 2 µl/cm$^2$ --
Line 27, replace "... of he harmful effects..." by -- .. of the harmful effects... --

Column 5,
Line 41, replace "2ml/cm$^2$" by -- 2 µl/cm$^2$ --

Column 7,
Line 10, replace "2ml/cm$^2$" by -- 2 µl/cm$^2$ --
Line 63, replace "In FIG. 2, CPD was ... by -- In FIG. 4, pyrimidine (6-4)pyrimidane photoproducts were... --
Lines 66 and 67, put "Quantitatively, these CPD products are summarized in Table 2" on line 63, just after "hot piperidine".

Signed and Sealed this

Twenty-second Day of July, 2003

JAMES E. ROGAN
*Director of the United States Patent and Trademark Office*